(12) United States Patent
Dorawa et al.

(10) Patent No.: US 9,888,939 B2
(45) Date of Patent: Feb. 13, 2018

(54) DEVICE AND METHOD FOR PREPARING A RECESS IN A BONE

(71) Applicants: Woodwelding AG, Stansstad (CH); Stryker European Holdings I, LLC, Kalamazoo, MI (US)

(72) Inventors: Klaus Dorawa, Schoenkirchen (DE); Urs Weber, Ramona, CA (US); Philipp Seiler, Arboldswil (CH); Laurent Torriani, Lamboing (CH)

(73) Assignees: Woodwelding AG (CH); Stryker European Holdings I, LLC, Kalamazoo, MI (US)

( * ) Notice: Subject to any disclaimer, the term of this patent is extended or adjusted under 35 U.S.C. 154(b) by 161 days.

(21) Appl. No.: 14/525,537

(22) Filed: Oct. 28, 2014

(65) Prior Publication Data

US 2015/0045838 A1   Feb. 12, 2015

Related U.S. Application Data

(62) Division of application No. 12/148,678, filed on Apr. 21, 2008, now abandoned.

(Continued)

(51) Int. Cl.
*A61B 17/86* (2006.01)
*A61B 17/3205* (2006.01)
(Continued)

(52) U.S. Cl.
CPC .... *A61B 17/32053* (2013.01); *A61B 17/1604* (2013.01); *A61B 17/864* (2013.01);
(Continued)

(58) Field of Classification Search
CPC .......... A61B 17/864; A61B 2017/0004; A61B 17/320068; A61F 2210/0004
(Continued)

(56) References Cited

U.S. PATENT DOCUMENTS

| 4,828,445 A | 5/1989 | Giannuzzi |
|---|---|---|
| 5,993,477 A | 11/1999 | Vaitekunas et al. |

(Continued)

FOREIGN PATENT DOCUMENTS

| DE | 10301023 | 7/2004 |
|---|---|---|
| WO | 2004089227 | 10/2004 |
| WO | 2006059120 | 6/2006 |

OTHER PUBLICATIONS

Annual Report 2002 of IBMT Fraunhofer, pp. 80, 81.
www.hielscher.com/ultrasonic/glossary.htm.

*Primary Examiner* — Anu Ramana
(74) *Attorney, Agent, or Firm* — Lerner, David, Littenberg, Krumholz & Mentlik, LLP

(57) ABSTRACT

A punching device for preparing a recess in a bone has a punching tool usable for such a punching device. An implant usable with the punching tool is provided and a method for preparing a recess in a bone are disclosed. The punching device comprises an ultrasonic sonotrode and a punching tool which is fixable to the sonotrode at its proximal extremity. At its distal extremity, the punching tool has a thin-walled portion having a non-rotational symmetric cross-section. By ultrasonic vibration of the punching tool, the thin-walled portion can be forced into a bone thereby preparing a recess of which is not rotationally symmetric. Subsequently, an implant can be held in such recess. Due to its lack of rotational symmetry, the implant may absorb rotational forces around its longitudinal axis.

19 Claims, 2 Drawing Sheets

Related U.S. Application Data

(60) Provisional application No. 60/926,884, filed on Apr. 30, 2007.

(51) Int. Cl.

| | | |
|---|---|---|
| *A61B 17/16* | (2006.01) | |
| *A61B 17/88* | (2006.01) | |
| *A61B 10/02* | (2006.01) | |
| *A61B 17/00* | (2006.01) | |
| *A61B 17/32* | (2006.01) | |

(52) U.S. Cl.
CPC ........ *A61B 17/8894* (2013.01); *A61B 10/025* (2013.01); *A61B 17/320068* (2013.01); *A61B 2017/00004* (2013.01); *A61B 2017/00371* (2013.01); *A61B 2017/320072* (2013.01)

(58) Field of Classification Search
USPC .................................. 606/169–171
See application file for complete search history.

(56) References Cited

U.S. PATENT DOCUMENTS

| | | |
|---|---|---|
| 6,090,998 A | 7/2000 | Grooms et al. |
| 6,485,495 B1 | 11/2002 | Jenkinson |
| 6,921,264 B2 | 7/2005 | Mayer et al. |
| 6,955,540 B2 | 10/2005 | Mayer et al. |
| 7,008,226 B2 | 3/2006 | Mayer et al. |
| 7,335,205 B2 | 2/2008 | Aeschlimann et al. |
| 7,765,672 B2 | 8/2010 | Clinch et al. |
| 2003/0050574 A1 | 3/2003 | Krueger |
| 2003/0078660 A1* | 4/2003 | Clifford ................ A61B 17/82 623/17.11 |
| 2003/0167072 A1 | 9/2003 | Oberlander |
| 2004/0102782 A1 | 5/2004 | Vercellotti et al. |
| 2004/0243129 A1 | 12/2004 | Moumene et al. |
| 2005/0222619 A1 | 10/2005 | Dreyfuss et al. |
| 2006/0105295 A1 | 5/2006 | Mayer et al. |
| 2006/0122543 A1 | 6/2006 | Mayer et al. |
| 2006/0235519 A1 | 10/2006 | Michelson |
| 2007/0095178 A1 | 5/2007 | Schraga |
| 2007/0265622 A1 | 11/2007 | Aeschlimann et al. |
| 2007/0265704 A1 | 11/2007 | Mayer et al. |
| 2007/0270974 A1 | 11/2007 | Aeschlimann et al. |
| 2008/0045961 A1 | 2/2008 | Aeschlimann et al. |
| 2008/0109080 A1 | 5/2008 | Aeschlimann et al. |
| 2008/0275500 A1 | 11/2008 | Aeschlimann et al. |
| 2009/0018560 A1 | 1/2009 | Mayer et al. |
| 2009/0317768 A1 | 12/2009 | Mayer et al. |

\* cited by examiner

DEVICE AND METHOD FOR PREPARING A RECESS IN A BONE

CROSS REFERENCE TO RELATED APPLICATION

This application is a divisional of U.S. patent application Ser. No. 12/148,678, filed Apr. 21, 2008 and U.S. Provisional Patent Application No. 60/926,884 filed Apr. 30, 2007, the disclosures of which are hereby incorporated herein by reference.

BACKGROUND OF THE INVENTION

The invention relates to preparing recesses or holes in bones of humans or animals. In such recesses or holes implants e.g. in the form of screws may be introduced. Such screws may be used for example to treat fractures of bones.

Conventionally, the recesses were generally drilled with a rotating tool and both the recesses and the screws or pins to be inserted therein usually have a circular cross-section. Due to this circular cross-section, a single recess-screw-combination is not suitable to accommodate rotation forces applied around the axis of the screw. In order to accommodate such rotation forces which may occur for example when fixing two parts of bones together or when fixing an implant to a bone, it has been necessary to provide a plurality of screws or pins inserted into a plurality of recesses prepared in the bone.

The necessity of preparing a plurality of recesses in a bone for example during a surgical intervention requires additional work for a physician. Furthermore, the preparation of a plurality of recesses in a bone may increase the discomfort for a patient and may delay the healing.

SUMMARY OF THE INVENTION

One aspect of the present invention is to provide a punching device for preparing a recess in a bone, a punching tool adapted to be used in such punching device or an implant adapted to be used as a punching tool for such punching device. A method is also disclosed for preparing a recess in a bone wherein the necessity of preparing a plurality of recesses can be avoided when an implantation device is to be inserted into a bone such that it can accommodate rotational forces between it and the bone.

These needs may be met by a punching device, a punching tool, an implant and a method for preparing a recess in a bone according to punching device for preparing a recess in a bone. The punching device comprises: an ultrasonic sonotrode, a punching tool being fixable to the sonotrode at its proximal extremity, wherein, at its distal extremity, the punching tool has a thin-walled portion having a cross section not being rotationally symmetric. The thin-walled portion preferably has a wall thickness (t) of less than 2 mm and may have an annular cross section. The thin-walled portion annular cross section may have a non-symmetric cross section. The punching tool may be made of a biocompatible or bioabsorbable material. The punching device thin-walled portion can have a lateral surface providing a high surface friction. An ultrasonic generator is adapted to excite the punching tool with a vibration frequency of between 10 kHz and 100 kHz and a vibration amplitude of between fpm and 300 μm. A punching tool usable for preparing a recess in a bone, wherein the punching tool is adapted to be used in a punching device as described above. An implant is inserted into a bone, wherein the implant is adapted to be used as a punching tool for a punching device. A method is used for preparing a recess in a bone, the method comprising: providing a punching device; abutting the punching tool on the bone; vibrating the punching tool with ultrasonic vibrations and pushing the punching tool into the bone. The method includes the step of removing the punching tool from the bone and releasing the punching tool from the sonotrode.

According to an aspect of the present invention a punching device for preparing a recess in a bone comprises an ultrasonic sonotrode and a punching tool being fixable to the sonotrode at its proximal extremity. Therein, the punching tool has a thin-walled portion at its distal extremity.

In the following, further features, advantages and embodiments of the punching device according to the first aspect will be explained in detail.

An ultrasonic sonotrode is a mechanical component which is adapted to transmit ultrasonic vibrations emitted by an ultrasonic generator to a tool which may be fixed to the ultrasonic sonotrode. For this purpose, the sonotrode can comprise a mechanism for fixedly coupling the sonotrode to an ultrasonic generator and a mechanism for coupling a tool to be vibrated to the sonotrode. In another embodiment, the punching tool may be axially slidable in relation to the ultrasonic sonotrode and the vibrating sonotrode may "hammer" onto the tool.

The punching tool is adapted to be fixed to the sonotrode at its proximal extremity. For example, the punching tool can be an elongated member. It may have a sufficient rigidity to transmit ultrasonic vibrations from its proximal extremity to its distal extremity.

At its distal extremity, the punching tool has a thin-walled portion. The thin-walled portion may be for example, a portion, where, in the cross-section of the thin-walled portion, a dimension in one direction of the thin-walled portion is substantially larger, for example three times larger, preferably ten times larger, than a dimension in a direction perpendicular thereto. The thin-walled portion of the punching tool can have a linear or a curved cross-section.

The thin-walled portion may have a non-rotational symmetric cross-section, i.e. a cross-section having no rotational symmetry. In other words, the two-dimensional geometry of the cross-section of the thin-walled portion can not be described by rotation of any one-dimensional pattern. Preferably, the cross-section is non-round. Therein, the cross-section is taken in a plane normal to the longitudinal axis of the punching tool.

The present invention is based on the idea that by using the punching tool which is fixedly coupled to an ultrasonic sonotrode which itself is coupled to an ultrasonic generator such that ultrasonic vibrations can be transmitted to the distal extremity of the punching tool, a recess of arbitrary circumferential geometry can be created within a bone. For this purpose, as will be described further below, the punching tool may be abutted against the bone and the vibrating punching tool may be pushed into the bone. Therein, the ultrasonic vibrations on the punching tool may act as little hammer blows whereby the punching tool may be forced into the bone. In order to generate a high pressure between the punching tool and the bone, the punching tool has a thin-walled portion such that the contact area between the punching tool and the bone is kept small.

As the thin-walled portion of the punching tool has a non-rotationally symmetric cross-section, the recess in the bone prepared thereby will have a non-rotationally symmetric cross-section. In such non-rotationally symmetric recess a corresponding non-rotationally symmetric implant may be press-fitted for positive fitting within the recess. As the implant and the recess have non-rotationally symmetric cross-sections rotational forces acting around the longitudinal axis of the implant may be absorbed by the implant and it may not be necessary to prepare a plurality of recesses in the bone in order to absorb such rotational forces.

According to an embodiment of the invention the thin-walled portion has a wall thickness of less than 2 mm, preferably less than 1 mm and more preferred between 0.2 and 0.5 mm. The smaller the thickness of the thin-walled portion the higher the pressure which can be applied by the punching tool onto the bone. However, the thickness of the thin-walled portion should be sufficient in order to provide sufficient stability for the thin-walled portion during preparing the recess in the bone such that the thin-walled portion does not deform or deflect during the process of preparing the recess and the vibration from the sonotrode is reliably transmitted to the contact area between punching tool and bone.

According to a further embodiment of the present invention the thin-walled portion has an annular cross-section. In other words, the thin-walled portion may have a self-contained, ring-like closed structure which, however, preferably should not have a circular cross-section. For example, the thin-walled portion may have the form of a hollow triangle, a hollow rectangle or any other hollow polygon.

According to a further embodiment of the present invention the thin-walled portion has a non-symmetric cross-section. This lack of symmetry, i.e. lack of mirror symmetry or lack of point symmetry or both, can be used to align an implant to be inserted into the recess in a predetermined way. Accordingly, already when preparing the recess in the bone an orientation of the implant to be fitted therein may be predetermined.

According to another embodiment, the punching tool comprise a metallic material. E.g. any kind of stainless steel, titanium alloys, aluminium alloys such as Ti6Al4v, APX, 1.4057, 1.4442, etc can be used. Bio-compatible metals are preferably used. Such bio-compatible material can be used for the punching tool in order to avoid interferences from occurring when punching a recess into a bone.

According to a further embodiment, the punching tool comprises a polymeric material. E.g. any kind of thermoplastic material such as e.g. PEEK (Polyetheretherketone), UHMWPE (Ultra high molecular weight polyethylene), and bioabsorbable materials such as PLA (Polylactic acid), PLLA (Poly-L-lactide), PLDLA (Poly(D,L-Lactid)), PDLLA (Poly-DL-lactide), PVDF (Polyvinylidene Difluoride), PPSU or ABS may be used. Such punching tools made with a bio-resorbable material can be used both for punching the recess into the bone and later on as an implant to remain in the prepared recess. Therein, after preparing the recess, the punching tool can be released from the ultrasonic sonotrode. It can remain in the prepared recess and after a predetermined period for healing, be resorbed in the bone.

According to another embodiment, the thin-walled portion of the punching tool has a lateral surface providing a high surface friction. For example, in a thin-walled portion having an annular cross-section it may be advantageous to provide the inner surface of the thin-walled portion such that high surface friction is obtained e.g. by providing this surface with a suitable surface geometry such as for example an increased roughness or by providing this surface with a material having a high coefficient of friction. Using such punching tool the punching tool may be first forced into the bone thereby preparing a recess in the form of the annular cross-section. Subsequently, when withdrawing the punching tool from the bone, the thin-walled portion having such high surface friction on its inner surface may entrain the bone portion located within the annular thin-walled portion, thereby preparing a complete hole comprising both the annular cross-section and the area therein. Accordingly, with such punching device a recess can be prepared in a bone the cross-section of which is substantially larger than the cross-section of the thin-walled portion of the punching tool.

According to a further embodiment of the present invention, the punching device further comprises an ultrasonic generator. This ultrasonic generator may be suitably adapted to be coupled with the ultrasonic sonotrode such that ultrasonic vibrations may be transmitted from the generator to the sonotrode.

In a further embodiment the ultrasonic generator is adapted to excite the punching tool with a vibration frequency of between 10 kHz and 100 kHz, preferably between 20 kHz and 40 kHz.

According to a further embodiment the ultrasonic generator is adapted to excite the punching tool with a vibration amplitude of between 1 μm and 300 μm, preferably between 5 μm and 100 μm. The vibration amplitude is defined in a direction perpendicular to the initial contact surface between the thin-walled portion of the punching tool and the bone, this being usually a longitudinal direction of the punching tool. The vibration amplitude might be selected taking into account the kind of bone into which a recess is to be introduced. For example, in weak bones a small vibration amplitude of e.g. 5 μm might be advantageous in order not to excessively stress such bones whereas in strong bones a higher vibration amplitude of e.g. 100 μm might be advantageous as the recess can be prepared faster.

A further aspect of the present invention is directed to a punching tool being usable for preparing a recess in a bone wherein the punching tool is adapted to be used in a punching device according to the first aspect described above.

Such a punching tool may be provided independently from the ultrasonic sonotrode. However, the sonotrode and the punching tool should be adapted such that they can be coupled together such that ultrasonic vibrations can be transmitted from the sonotrode to the punching tool. A plurality of punching tools having different geometry in their thin-walled portions may be provided such that a physician can choose a suitable punching tool during an operation and also may release and replace a punching tool during an operation.

In a further aspect of the invention an implant to be inserted into a bone is provided wherein the implant is adapted to be used as a punching tool for the inventive punching device as described above. Such implant should satisfy two requirements: (a) On the one hand it should be sufficiently rigid to be used as a punching tool for preparing a recess in a bone; (b) on the other hand it should have a suitable material and/or geometry in order to be able to remain in the recess previously prepared therewith.

In a further aspect of the invention a method for preparing a recess in a bone is provided, the method comprising: providing a punching device according to the above first aspect; abutting the punching tool of the punching device on the bone; vibrating the punching tool with ultrasonic vibrations and pushing the punching tool into the bone.

According to an embodiment, the punching tool can be removed from the bone after preparing the recess. Thereby, a recess may be prepared in the bone into which an implant can subsequently be inserted.

According to another embodiment the punching tool may be released from the sonotrode after pushing it into the bone and the punching tool may remain in the prepared recess as an implant.

It has to be noted that embodiments of the invention are described with reference to different subject-matters. In particular, some embodiments are described with reference to apparatus type claims whereas other embodiments are described with reference to method type claims. However, a person skilled in the art will gather from the above and the following description that, unless other notified, in addition to any combination of features belonging to one type of subject-matter also any combination between features relating to the different subject-matters, in particular between features of the apparatus type claims and features of the method type claims, is considered to be disclosed with this application.

The aspects defined above and further aspects, features and advantages of the present invention can be derived from the examples of embodiments described hereinafter.

The invention will be described in more detail hereinafter with reference to examples of embodiments but to which the invention is not limited.

BRIEF DESCRIPTION OF THE DRAWINGS

In the figures like reference signs designate like elements. Furthermore, it is to be noted that the figures are not to scale.

DETAILED DESCRIPTION

Figure 1:
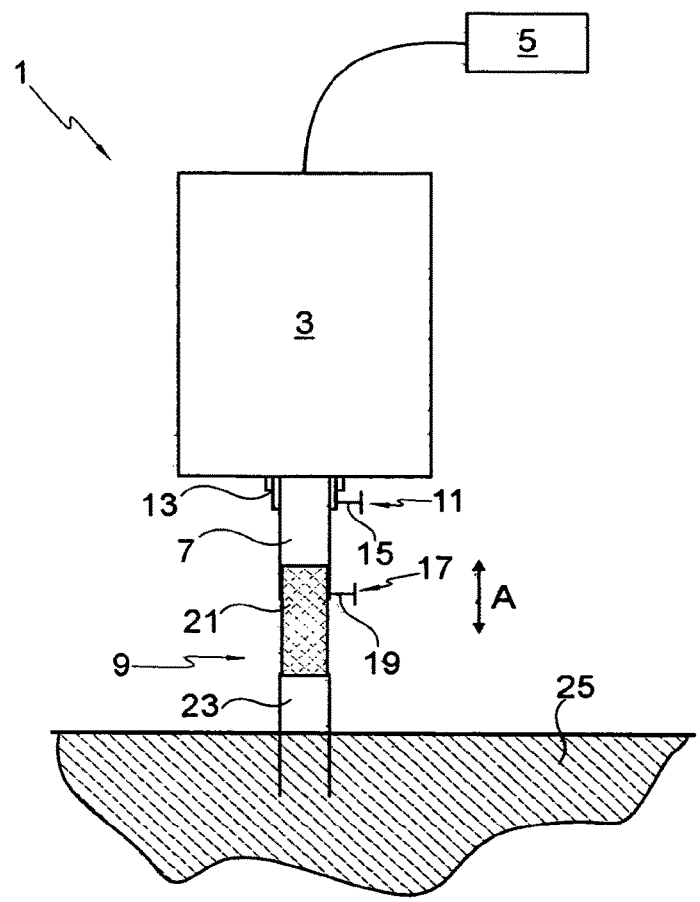
FIG. 1 schematically shows a punching device according to an embodiment of the invention.

As schematically shown in FIG. 1, a punching device according to an embodiment of the invention comprises an ultrasonic generator 3 controlled via a control 5, an ultrasonic sonotrode 7 and a punching tool 9.

The ultrasonic sonotrode 7 is coupled to the ultrasonic generator 3 via a fixation mechanism 11 which can comprise for example a frame 13 and a clamping screw 15. The ultrasonic generator 3 is adapted to emit ultrasonic vibrations with an adaptable frequency of e.g. 20 to 50 kHz which are transmitted to the sonotrode 7. The arrow A in FIG. 1 indicates a direction of these ultrasonic vibrations. Furthermore, the ultrasonic generator 3 may be adapted to produce ultrasonic vibrations with a selectable amplitude of between 5 and 100 µm along the direction A.

The punching tool 9 is coupled to the ultrasonic sonotrode 7 via a further fixation mechanism 17 which can comprise a clamping screw 19. Thereby, the ultrasonic vibrations can be transmitted from the sonotrode to the punching tool. The punching tool 9 comprises at its proximal extremity a solid portion 21 and at its distal extremity a thin-walled portion 23. The thin-walled portion 23 can have a non-round cross-section as will be described further below with reference to FIGS. 3a to 3e.

When the punching tool being vibrated via the sonotrode is pushed onto a bone 25, the thin-walled portion 23 exerts a significant pressure onto the bone while being vibrated up and down in a hammer-like manner. Due to this ultrasonic "hammering" the thin-walled portion 23 of the punching tool 9 can be introduced into the bone. In contrast to conventional drilling methods, there is no rotating of the punching tool such that the recess which is prepared by the punching device does not need to have a rotational geometry.

Figures 2A, 2B:
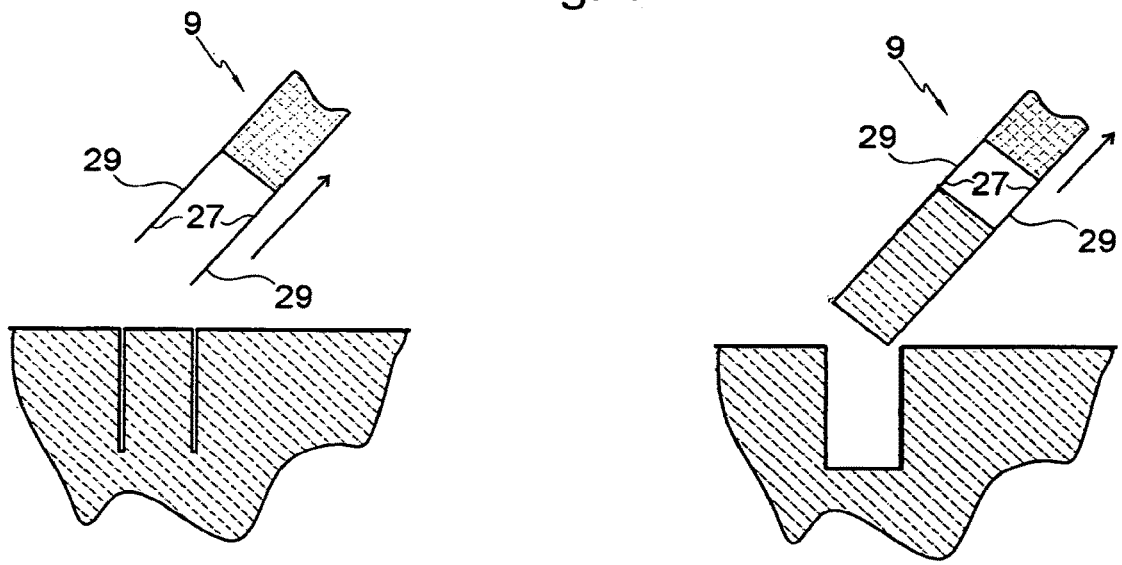
FIGS. 2a and 2b show embodiments of the punching device and different uses thereof according to the invention.

FIGS. 2a and 2b show different embodiments of punching tools usable for preparing recesses of different cross-sectional areas in a bone. In FIG. 2a, the lateral surfaces 27, 29 of the thin-walled portion of the punching tool 9 both have a low surface friction. Accordingly, the punching tool 9 can be easily withdrawn from the bone after preparing the recess in the bone. The recess itself then has a cross-section which essentially corresponds to the cross-section of the thin-walled portion. Accordingly, the portion of an implant to be inserted into the recess should approximately have the geometry as the thin-walled portion of the punching tool. Alternatively, the punching tool itself can act as such implant and can remain in the recess after preparing the recess.

Alternatively, as shown in FIG. 2b, the thin-walled portion of the punching tool 9 can have a low surface friction on its outer lateral surface 29 whereas it can have a high surface friction at its inner lateral surface 27. Accordingly, after preparing the recess in the bone by ultrasonic "hammering" the thin-walled portion into the bone, when removing the punching tool from the bone, a part of the bone lying between the inner lateral surfaces 27 of the thin-walled portion can be removed therewith due to the high surface friction. Subsequently, a massive implant can be press-fitted into the large-area recess.

Figure 3A:
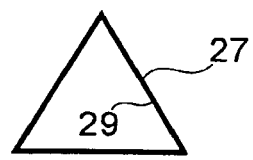
FIGS. 3a to 3e show different cross-sectional geometries of the thin-walled portion of the punching tool according to embodiments of the invention.
Figure 3B:
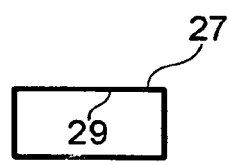
Figure 3C:
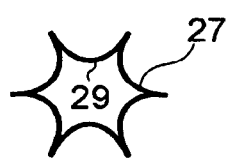
Figure 3D:
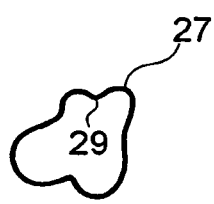

In FIGS. 3a to 3e several possibilities for the cross-section of the thin-walled portion of the punching tool are schematically shown. FIG. 3a shows a triangular cross-section. FIG. 3b shows a rectangular cross-section. FIG. 3c shows a star-like cross-section. FIG. 3d shows an arbitrary non-symmetric cross-section. All of the cross-sections for the thin-walled portion shown in FIGS. 3a to 3d include a closed annular cross-section having an inner lateral surface 29 and an outer lateral surface 27.

Figure 3E:

The cross-section shown in FIG. 3e is serpent-like and has no annular cross-section. Furthermore, a wall thickness (t) of the thin-walled portion is shown.

All of the cross-sections for the thin-walled portion of the punching tools shown in FIGS. 3a to 3e have no rotational symmetry and are therefore suitable to prepare a corresponding non-rotationally symmetric recess in a bone in which an implant can be inserted which then is able to absorb a rotational force around the longitudinal axis of the punching device.

Summarizing, a punching device for preparing a recess in a bone, a punching tool usable for such punching device 1, an implant usable with such punching tool and a method for preparing a recess in a bone are proposed. The punching device comprises an ultrasonic sonotrode 7 and a punching tool 9 which is fixable to the sonotrode at its proximal extremity. At its distal extremity, the punching tool 9 has a thin-walled portion 23 having a rotationally non-symmetric cross-section. By ultrasonic vibration of the punching tool, the thin-walled portion can be forced into a bone thereby preparing a recess which is not rotationally symmetric. Subsequently, an implant can be held in such recess. Due to its lack of rotational symmetry, the implant may absorb rotational forces around its longitudinal axis.

It should be noted that the term "comprising" does not exclude other elements or steps and the "a" or "one" does not exclude a plurality. Also elements described in association with different embodiments and aspects may be combined. It should also be noted that reference signs in the claims shall not be construed as limiting the scope of the claims.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An implant to be inserted into a bone, comprising a proximal end portion and a distal end portion, the distal and proximal end portions extending along a longitudinal axis;
   wherein the proximal end portion of the implant is solid and is fixable to an ultrasound sonotrode of a punching tool;
   wherein the distal end portion of the implant comprises a continuous thin wall extending between concentric exterior and interior surfaces surrounding a hollow interior and forming a hollow open bone facing end for contacting bone;
   wherein the exterior and interior surfaces defining the thin-wall of the distal end portion define a non-symmetric circumference surrounding the hollow interior in a direction perpendicular to the longitudinal axis;
   wherein the non-symmetric circumference of the thin-wall of the distal end portion extends along a longitudinal extent of the hollow thin-wall of the distal end portion including the hollow open bone facing end; and
   the implant being adapted to be used as a punching tool for a punching device and being capable of forming a slot in a bone for anchoring the implant in the bone.

2. The implant according claim 1, wherein the thin-walled portion has a wall thickness (t) of less than 2 mm.

3. The implant according to claim 1, wherein the implant comprises a bio-compatible material.

4. The implant according to claim 3, wherein the bio-resorbable material is material selected from the group consisting of PLA (Polylactic acid), PLLA (Poly-L-lactide), PLDLA (Poly (D,L-lactid)), PDLLA (Poly-DL-lactide).

5. The implant according to claim 1, wherein the thin-walled portion has a lateral surface providing a high surface friction.

6. A system comprising:
   the implant according to claim 1 in combination with an ultrasonic generator.

7. The system according to claim 6, wherein the ultrasonic generator is adapted to excite the implant when used as a punching tool with a vibration frequency of between 10 kHz and 100 kHz.

8. The system according to claim 6, wherein the ultrasonic generator is adapted to excite the punching tool with a vibration amplitude of between 1 μm and 300 μm.

9. A method for inserting an implant into a bone, the method comprising:
   providing a system according to claim 6;
   fixing the implant to an ultrasound sonotrode of the ultrasonic generator;
   abutting the bone facing end of the implant on the bone;
   vibrating the implant with ultrasonic vibrations and pushing the implant so as to prepare a slot in the bone for receiving the implant; and
   releasing the implant from the sonotrode.

10. An implant for insertion into a closed circumference non-symmetric recess formed in a bone comprising:
    a body having a longitudinal axis;
    the body having a solid proximal portion connectable to an ultrasonic sonotrode and a longitudinally extending thin-walled distal portion having a continuous closed circumference enclosing a hollow interior, the thin-wall defined by concentric inner and outer surfaces, the inner surface surrounding the hollow interior of the body, the thin-walled portion having a non-symmetric circumference matching the non-symmetric recess formed in the bone and the thin-walled distal portion defining a non-symmetrical end face extending between the concentric inner and outer surfaces of the body for insertion into the recess, the end face being completely open to the hollow interior at an end of the thin-walled distal portion facing the bone; and
    wherein the implant body solid proximal portion is made completely of a bio-resorbable material.

11. The implant according claim 10, wherein the implant body thin-walled portion has a wall thickness (t) of less than 2 mm.

12. The implant according to claim 10, wherein the implant body thin-walled portion has a continuous circumferential end face which has a non-symmetrical shape in a direction transverse to the longitudinal axis of the body.

13. The implant as set forth in claim 10, wherein the thin-walled portion has outer surfaces providing a high surface friction upon vibration by the ultrasonic sonotrode.

14. The implant according to claim 10, wherein the bio-resorbable material is material selected from the group consisting of PLA (Polylactic acid), PLLA (Poly-L-lactide), PLDLA (Poly (D,L-lactid)), PDLLA (Poly-DL-lactide).

15. An implant for insertion into a non-symmetric recess in a bone, the recess formed by the implant, the implant comprising:
    a longitudinally extending body adapted to be used as a tool for forming a recessed closed circumference opening in a bone, the body, at a proximal portion of the body is solid and is fixable to an ultrasonic sonotrode, wherein a distal portion of the body has a portion with a thin-wall extending about a longitudinal axis of the body, the thin-wall defined by concentric interior and exterior surfaces of the body, the thin-wall has a non-symmetric outer circumference, including a non-symmetric end face extending between the interior surface and the exterior surface, wherein the implant comprises a bio-resorbable material, the distal portion having a hollow interior enclosed by the interior surface of the thin-wall open at a distal bone facing end of the distal portion, and the non-symmetric hollow end face for contacting bone, the non-symmetric end face of the thin wall located around a perimeter spaced from and transverse to the longitudinal axis of the distal portion.

16. A method for forming a recess in a bone using the implant of claim 15, the method comprising:
    providing the implant of claim 15;
    contacting the bone with the implant;
    mounting a sonotrode producing ultrasonic vibrations on the proximal portion of the body; and
    vibrating the implant with ultrasonic vibrations and pushing the implant into the bone.

17. The implant according claim 15, wherein the thin-walled portion has a wall thickness (t) of less than 2 mm.

18. The implant according to claim 17 wherein the implant comprises a bio-resorbable material.

19. The implant according to claim 18, wherein the bio-resorbable material is material selected from the group consisting of PLA (Polylactic acid), PLLA (Poly-L-lactide), PLDLA (Poly (D,L-lactid)), PDLLA (Poly-DL-lactide).

\* \* \* \* \*